United States Patent
Lan-Hargest et al.

(10) Patent No.: US 6,720,445 B2
(45) Date of Patent: Apr. 13, 2004

(54) ACETYLOXYMETHYL ESTERS AND METHODS FOR USING THE SAME

(75) Inventors: Hsuan-Yin Lan-Hargest, Fallston, MD (US); Norbert L. Wiech, Phoenix, MD (US)

(73) Assignee: Beacon Laboratories, Inc., Phoenix, MD (US)

(*) Notice: Subject to any disclaimer, the term of this patent is extended or adjusted under 35 U.S.C. 154(b) by 0 days.

(21) Appl. No.: 09/742,727

(22) Filed: Dec. 21, 2000

(65) Prior Publication Data

US 2002/0161045 A1 Oct. 31, 2002

(51) Int. Cl.$^7$ .................. C07C 323/04; C07C 323/03; C07C 323/06; C07C 321/16; C07C 69/76
(52) U.S. Cl. .................. 560/15; 560/51; 560/55; 560/147; 560/152; 560/179; 560/183; 560/205; 560/231; 560/8; 560/17; 560/104; 560/1; 514/533; 514/529
(58) Field of Search .................. 560/8, 51, 55, 560/147, 152, 179, 183, 205, 231, 15, 17, 104, 1; 514/533, 529

(56) References Cited

U.S. PATENT DOCUMENTS

| | | | |
|---|---|---|---|
| 3,089,883 A | | 5/1963 | Dohr et al. |
| 4,900,478 A | * | 2/1990 | Gross .................. 260/408 |
| 5,055,588 A | | 10/1991 | Takase et al. |
| 5,158,773 A | * | 10/1992 | Gross .................. 424/401 |
| 5,173,506 A | | 12/1992 | Neustadt et al. |
| 5,200,553 A | | 4/1993 | Nudelman et al. |
| 5,569,675 A | | 10/1996 | Rephaeli et al. |
| 5,574,097 A | * | 11/1996 | Klaveness et al. .......... 525/61 |
| 5,626,855 A | | 5/1997 | Philippe |
| 5,667,962 A | | 9/1997 | Brunengraber et al. |
| 5,674,468 A | * | 10/1997 | Klaveness et al. |
| 5,710,176 A | | 1/1998 | Rephaeli et al. |
| 5,710,279 A | | 1/1998 | Lantzsch et al. |
| 5,939,455 A | | 8/1999 | Rephaeli |
| 6,040,342 A | | 3/2000 | Rephaeli et al. |
| 6,071,923 A | | 6/2000 | Nudelman et al. |
| 6,110,955 A | | 8/2000 | Nudelman et al. |
| 6,110,970 A | | 8/2000 | Nudelman et al. |

FOREIGN PATENT DOCUMENTS

| | | | |
|---|---|---|---|
| DE | 32 07 241 A | | 9/1983 |
| EP | 250997 | * | 7/1988 |
| GB | 1 138 745 A | | 1/1969 |
| GB | 2 043 639 A | | 10/1980 |
| GB | 1 579 531 A | | 11/1980 |
| GB | 2 048 857 A | | 12/1980 |
| GB | 2 097 786 A | | 11/1982 |
| JP | 57 179190 A | | 11/1982 |
| JP | 60 139682 A | | 7/1985 |
| WO | WO01/90136 A | | 7/1985 |
| WO | WO98/00127 A | | 1/1998 |
| WO | WO98/39965 A | | 9/1998 |
| WO | WO98/40065 A | | 9/1998 |

OTHER PUBLICATIONS

M. Altamura et al, "Zinc Mediated Reduction of Bromohydrins in Azetidinones and Penems. Application to the Synthesis of FCE 22891", Heterocycles, vol. 32 (1991), pp. 1671–1679.*

Lombardi et al., "Total Synthesis of Thia Analogues of Clavulanic Acid," Tetrahedron Letters, 39, 1979, 3777–3780.

Foglio et al., "Synthesis of Opitcally Active (5R)–2–Penem–3–carboxylates from penicillanic Acide Derivatives: New Potent Anti–bacterial Agents," J.C.S. Chem. Commun. 2, 1980, 70–71.

Drew et al., "Antifertility of N–Protected Glycine Activated Esters," J. Pharma. Sci., 70, 1981, 60–63.

Longo et al., "Total Synthesis and Antibacterial Activity of Some 6–Ethyl–2–penem Derivatives," Gazz. Chim. Ital., 111, 1981, 371–377.

Alpegiani et al., "Synthesis of 2–(Heterocyclylthiomethyl-)Penems," Gazz. Chim. Ital., 114, 1984, 319–324.

Battistini et al., "Synthesis of New Penem Derivatives: N–Substituted Analogs of FCE 22101," Heterocycles, 23, 1985, 1929–1932.

Heilporn et al., "Synthesis of BAPTA–AM Analogues Capable of Enhancing the Vascular Production of Prostacyclin," Bull. Soc. Chim. Belg., 104, 1994, 309–319.

Salazar et al., "Optically–active Dihydropyridines via Lipase–catalyzed Enantioselective Hydrolysis," Tetrahedron: Asymmetry, 6, 1995, 2917–2920.

* cited by examiner

Primary Examiner—Paul J. Killos
Assistant Examiner—M. P. Moon
(74) Attorney, Agent, or Firm—Fish & Richardson P.C.

(57) ABSTRACT

Novel acetyloxymethyl esters are disclosed. Methods of treating an illness, including cancer, hemological disorders and inherited metabolic disorders, and treating or ameliorating other conditions using these compounds are also disclosed. The compounds are effective in the inhibition of histone deacetylase.

9 Claims, 7 Drawing Sheets

ACETYLOXYMETHYL ESTERS AND METHODS FOR USING THE SAME

FIELD OF THE INVENTION

The present invention relates to novel acetyloxymethyl esters. The invention further relates to use of those acetyloxymethyl esters in the treatment of cancer and other proliferative diseases, hemoglobinopathies and inherited metabolic disorders and to treat or ameliorate various other illnesses and conditions, such as by hematopoietic stimulation. The present invention also relates to methods for using the disclosed compounds in the inhibition of histone deacetylase.

BACKGROUND INFORMATION

Histones are unique proteins in the nucleus of a cell. DNA is wound around a complex of histones to form nucleosomes. As such, histones are an integral structural element of the chromatin material. The histones complexed with the DNA are susceptible to a range of chemical modifications, one of which is acetylation, and the reverse of which is deacetylation. Acetylation of histone protein is believed to facilitate transcription of the DNA, thereby enhancing correlating with gene expression. Histone deacetylase is believed to reverse the process that represses gene expression. Histone dynamics are regulated by two enzymes—histone acetyl transferase and histone deacetylase.

Hyperacetylation due to inhibition of histone deacetylation, and the resulting expression of a latent gene, have been observed or proposed to occur in numerous inherited metabolic diseases and in cancer. The inhibition of histone deacetylase is believed to activate an otherwise dormant fetal gene, which serves as a redundant or back-up gene. Pharmacological inhibition of histone deacetylase, therefore, is believed to induce the expression of repressor genes in cancer tissue, inhibit the expression of tumor-promoting genes, and induce the expression of the redundant or back-up gene in patients suffering from various metabolic and hematological diseases. Thus, inhibition of histone deacetylase is proposed to slow the growth of neoplastic cells and/or reverse the deficient process of various metabolic and hematological diseases. Inhibition of histone deacetylase is also believed to play a role in antiprotozoal activity.

Trichostatin is the most potent inhibitor of histone deacetylase observed so far, but due to various drawbacks, such as availability of the material, has not been pursued.

Butyric acid is a natural product that has been known for several decades to be an effective differentiating and antiproliferative agent in a wide spectra of neoplastic cells in vitro. For example, butyric acid has been reported to induce cellular and biochemical changes in cancer cells, to induce apoptosis, and to increase the expression of transfected DNA, although the mechanism of action of butyric acid is unknown. Increased histone acetylation following treatment with butyric acid has been correlated with changes in transcriptional activity and at differentiated states of cells. Butyric acid and its salts, however, have shown low potency in both in vitro assays and clinical trials, and thus require large doses to achieve even minimal therapeutic effects. This can lead to fluid overload and mild alkalosis.

The present invention is directed to acetyloxymethyl ester compounds, and methods for using the same, that have also been found to inhibit histone deacetylase. The present compounds show significantly greater activity than butyric acid or its salts. That acetyloxymethyl esters such as those of the present invention have the ability to inhibit histone deacetylase has been previously unreported in the art.

SUMMARY OF THE INVENTION

The present invention relates to novel acetyloxymethyl esters as described below. The compounds are useful in the inhibition of histone deacetylase.

The present invention therefore further relates to methods of treating a patient for an illness, particularly wherein the illness is one in which histone deacetylase inhibition would be beneficial. Examples include cancer, hemoglobinopathies and inherited metabolic disorders. Other illnesses and conditions that can be treated according to the present invention are discussed herein. In the case of histone deacetylase inhibition, the present compounds are believed to function by chelating the zinc ion at the active site of histone deacetylase; the inventor does not wish to be bound by this mechanism, however.

It is therefore an aspect of the invention to provide novel acetyloxymethyl esters.

Another aspect of the invention provides methods for treating a patient using acetyloxymethyl esters.

A method for inhibiting histone deacetylase in a patient is also an aspect of the present invention.

These and other aspects of the invention will be apparent upon reviewing the attached specification and appended claims.

DETAILED DESCRIPTION OF THE INVENTION

The present invention is directed to acetyloxymethyl esters having the general formula (1):

(1)

wherein R is a substituted or unsubstituted $C_2$–$C_7$ alkenyl, a substituted or unsubstituted $C_2$–$C_7$ alkynyl, a cis or trans retinoyl group, or has the general formula (2):

(2)

wherein Z is selected from the group consisting of hydrogen and substituted or unsubstituted aryl, heteroaryl, cycloalkyl having the formula $C_nH_{2n-1}$, and alkoxy;

wherein n is 3 or greater;

wherein X is S, O, C=O or $CH_2$;

wherein $R_1$ is S, O, CH=CH or C≡C;

wherein $R_2$ is $CH_2$, CH=CH or C≡C; and wherein o, p and q are the same or different are each between 0 and 7, but when o is zero and $R_1$ or $R_2$ is CH=CH or C≡C, Z is not hydrogen or alkoxy.

A retinoyl group will be understood as being derived from retinoic acid and having general formula (3):

(3)

Preferred embodiments of formula 1 include the following:

phenylpropioloyloxymethyl acetate (wherein R is $C_6H_5$—C≡C—);

S-benzylthioglycoloyloxymethyl acetate (wherein R is $C_6H_5$—$CH_2$—S—$CH_2$—);

3-(phenylthio)acryloyloxymethyl acetate (wherein R is $C_6H_5$—S—CH=CH—.);

4-cyclohexanebutyroyloxymethyl acetate (wherein R is $C_6H_{11}$—$(CH_2)_3$—);

cinnamoyloxymethyl acetate (wherein R is $C_6H_5$—CH=CH—);

6-phenyl-3,5-hexadienoyloxymethyl acetate (wherein R is $C_6H_5$—$(CH=CH)_2$—$CH_2$—); and

5-phenyl-2,4-pentadienoyloxymethyl acetate (wherein R is $C_6H_5$—(CH=CH)—).

Pharmaceutically acceptable salts of any of the above compounds are also within the scope of the invention. As used herein, "pharmaceutically acceptable salts" refer to derivatives of the disclosed compounds that are modified by making acid or base salts. Examples include, but are not limited to, mineral or organic acid salts of basic residues such as amines, alkali or organic base salts of acidic residues such as carboxylic acids, and the like. Pharmaceutically acceptable salts include, but are not limited to, hydrohalides, sulfates, methanesulfates, toluenesulfonates, nitrates, phosphates, maleates, acetates, lactates and the like.

Pharmaceutically-acceptable salts of the compounds of the present invention can be prepared by reacting the free acid or base forms of these compounds with a stoichiometric or greater amount of the appropriate base or acid in water or in an organic solvent, or in a mixture of the two; generally, nonaqueous media like ether, ethyl acetate, ethanol, isopropanol, or acetonitrile are preferred. The salts of the invention can also be prepared by ion exchange, for example. Lists of suitable salts are found in *Remington's Pharmaceutical Sciences*, 18$^{th}$ ed., Mack Publishing Company, Easton, Pa. (1990).

The present invention is also directed to methods of treating illnesses in which proliferation of neoplastic or diseased cells occurs, or illnesses in which inhibition of histone deacetylase would be desired; as discussed above, inhibition of histone deacetylase results in the enhancement of gene expression that slows the growth of neoplastic cells and reverses the deficient process of various metabolic and hematological diseases. It will be understood that the present invention encompasses the treatment of various illnesses, as that term is defined herein, regardless of whether the treatment is through histone deacetylase inhibition, through another mechanism, or through a variety of mechanisms. The present compounds have a plasma half-life of sufficient length to effect a therapeutic benefit without requiring excessive doses, or doses that are toxic to a patient.

More specifically, the present invention is further directed to a method for treating an illness in a patient comprising administering to that patient an effective amount of a compound having general formula (1):

(1)

wherein R is substituted or unsubstituted $C_2$–$C_{10}$ alkenyl, substituted or unsubstituted $C_2$–$C_{10}$ alkynyl, a cis or trans retinoyl group, or has the general formula (2):

(2)

wherein Z is selected from the group consisting of hydrogen and substituted or unsubstituted aryl, heteroaryl, cycloalkyl having the formula $C_nH_{2n-1}$, and alkoxy;

wherein n is 3 or greater;

wherein X is S, O, C=O or $CH_2$;

wherein $R_1$ is S, O, CH=CH or C≡C;

wherein $R_2$ is $CH_2$, CH=CH or C≡C; and wherein o, p and q are the same or different are each between 0 and 10, but when o is zero and $R_1$ or $R_2$ is CH=CH or C≡C, Z is not hydrogen or alkoxy.

Illnesses treatable according to the present invention include, but are not limited to, various cancers, hematological diseases, and inherited metabolic diseases. Cancer includes, but is not limited to, leukemias, such as acute promyelocytic leukemia, acute myeloid leukemia, and acute myelomonocytic leukemia; other myelodysplastic syndromes; multiple myeloma such as breast carcinomas, cervical cancers, melanomas, colon cancers, nasopharyngeal carcinoma, non-Hodgkins lymphoma (NHL), Kaposi's sarcoma, ovarian cancers, pancreatic cancers, hepatocarcinomas, prostate cancers, squamous carcinomas, other dermatologic malignancies, teratocarcinomas, T-cell lymphomas, lung tumors, gliomas, neuroblastomas, peripheral neuroectodermal tumors, rhabdomyosarcomas, and prostate tumors and other solid tumors. Hematological diseases or hemoglobinopathies within the scope of the present invention include, but are not limited to, thalassemias, sickle cell anemias, infectious anemias, aplastic anemias, hypoplastic and hypoproliferative anemias, sideroblastic anemias, myelophthisic anemias, antibody-mediated anemias, anemias due to chronic diseases and enzyme-deficiencies, and anemias due to blood loss, radiation therapy and chemotherapy. Inherited metabolic diseases include, but are not limited to, Duschenne's muscular dystrophy, cystic fibrosis, and adrenoleukodystrophy. Thus, the term "illness" as used herein encompasses at least all of these things.

The term "illness" as used herein also encompasses various conditions such as cutaneous ulcers and gastrointestinal disorders. The cutaneous ulcers which can be treated in accordance with the current methods include leg and decubitus ulcers, stasis ulcers, diabetic ulcers and atherosclerotic ulcers. Gastrointestinal disorders treatable by the present methods include colitis, inflammatory bowel disease, Crohn's disease and ulcerative colitis. The term illness also refers to wounds such as abrasions, incisions, and burns.

"Illness" also encompasses treatment, prevention, or amelioration of virus-associated tumors including, but not limited to, EBV-associated malignancy, Kaposi's sarcoma, AIDS-related lymphoma, hepatitis B-associated malignancy or hepatitis C-associated malignancy. EBV-associated malignancy include, but are not limited to, nasopharyngeal carcinoma and non-Hodgkins' lymphoma. The present compounds can be administered in conjunction with a therapeutically effective amount of an antiviral agent such as ganciclovir, acyclovir and farnciclovir. Protozoan infections are also included within "illness" and include, for example, malaria, cryptosporidiosis, trypanosomiasis, Eimeria sp., Plasmodium sp., toxoplasmosis, and coccidiosis.

In another embodiment of this invention, "illness" refers to alopecia, or hair loss. Alopecia is a common condition that results from diverse causes. In particular, alopecia frequently occurs in cancer patients who are treated with chemotherapeutic drugs and/or irradiation. Such agents damage hair follicles which contain mitotically active hair-producing cells. Such damage may cause abnormally slow growth of the hair or may lead to frank loss. Thus, the present invention further relates to methods for protecting against injury to hair follicles in a patient by administering one or more of the present compounds to the patient.

"Patient" refers to members of the animal kingdom, including but not limited to humans. Preferably, the methods of the present invention are applied to a patient suffering from any of the illnesses listed above.

The compounds of the invention can be administered by any conventional means available for use in conjunction with pharmaceuticals, either as individual therapeutic agents or in combination with other therapeutic agents known in the art for the illness being treated. The compounds can be administered alone, but are generally administered with a pharmaceutically acceptable carrier selected on the basis of the chosen route of administration and standard pharmaceutical practice. The compositions of the invention may be adapted for oral, parenteral, topical, transdermal, transmucosal, rectal or intranasal administration, and may be in unit dosage form; the term "parenteral" as used herein includes subcutaneous, intravenous, intramuscular, or intrastemal injection or infusion techniques. Methods for preparing the present compositions for use by a patient are well known to those skilled in the pharmaceutical arts; formulations can include one or more fillers or preservatives in addition to the active ingredient and carrier.

"Pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Use of any of these media or agents is contemplated with the compounds of the present invention, absent compatibility problems with the active compound.

It is especially advantageous to formulate compositions in dosage unit form for ease of administration and uniformity of dosage. Dosage unit form as used herein refers to physically discrete units suited as unitary dosages for the patient to be treated, each unit containing a pre-determined quantity of active compound or "effective amount" calculated to produce the desired therapeutic effect in association with the pharmaceutical carrier. The specification for the dosage unit forms of the invention are dictated by and directly dependent on the characteristics of the active compound, the particular therapeutic effect to be achieved, and the limitations inherent in the art of compounding such an active compound for the treatment of sensitivity in individuals.

The appropriate dosage or "effective amount" administered in any given case will, of course, vary depending upon known factors, such as the pharmacodynamic characteristics of the particular compound and its mode and route of administration; the age, general health, metabolism, weight of the patient and other factors which influence response to the compound; the nature and extent of the illness being treated; the kind of concurrent treatment, if any; the frequency of treatment; and the effect desired. Generally, the effective amount will be that amount of the present compounds needed to inhibit histone deacetylase, without resulting in toxicity to the patient. Inhibition at any level is within the scope of the present invention and will contribute to a therapeutic benefit in a patient. A daily dosage of active ingredient will typically be between about 10 to 10,000 milligrams per meter$^2$ (mg/m$^2$) of body mass, with the preferred dose being 50–5,000 mg/m$^2$ body mass.

It will be appreciated that the therapeutic benefits of administration of the present compounds will be manifest in a variety of ways, depending on the patient and the illness being treated. More than one therapeutic benefit may be observed. The elicitation of any therapeutic benefit by the present methods is within the scope of the invention. "Treating" or "treatment" refers herein to both therapeutic and prophylactic treatments; for ease of reference, "therapeutic benefit" therefore refers collectively to both therapeutic and prophylactic benefits. Therapeutic benefits that may be achieved according to the present invention include, for example, retarding or eliminating tumor growth, apoptosis of tumor cells, healing wounds, healing cutaneous ulcers, ameliorating gastrointestinal disorders, modulating gene expression, inhibiting telomerase activity, inducing tolerance to antigens, preventing and/or ameliorating protozoan infection, inhibiting histone deacetylace in cells, modulating an immune response, ameliorating the effects of a cytotoxic agent, stimulating hematopoietic cells ex vivo and protecting hair follicles.

Modulation of an immune response can include, for example, enhancing cytokine secretion, inhibiting or delaying apoptosis in polymorphonuclear cells, enhancing polymorphonuclear cell function by augmenting hematopoietic growth factor secretion, inducing expression of cell surface antigens in tumor cells, and enhancing progenitor cell recovery after bone marrow transplantation.

Ameliorating the effects of a cytotoxic agent involves administering the present compounds in conjunction with the cytotoxic agent in such an amount so as to induce growth arrest of rapidly-proliferating epithelial cells of the patient, thereby protecting them from the cytotoxic effects of the agent. Cytotoxic agents, include, for example, chemotherapeutic agents, anticancer agents, and radiation therapy.

Modulating gene expression can be used to enhance, augment or repress the expression of a gene of interest. When expression of the gene of interest is to be enhanced or augmented, the gene can encode a gene product that is or acts as a repressor of another gene, a tumor suppressor, an inducer of apoptosis or an inducer of differentiation. Enhancing recombinant gene expression can be effected in a number of cells; the gene product can be any protein or peptide of interest such as tumor suppression genes. When expression of the gene of interest is to be repressed, the gene can encode a gene product that is or acts as an oncogene or an inhibitor of apoptosis, such as the bcl2 gene.

Inhibition of telomerase activity in cancer cells inhibits the malignant progression of the cells.

Inducing tolerance to an antigen is preferably carried about with a self-antigen, such as those associated with an autoimmune disease such as systemic lupus erythromatosus, rheumatoid arthritis, multiple sclerosis or diabetes. Tolerance can also be induced to one or more antigens present on a transplanted organ or cells.

The present invention is also directed a pharmaceutical composition comprising the compounds of formula 1 within a pharmaceutically acceptable carrier.

EXAMPLES

The following examples are intended to illustrate the invention, and should not be construed as limiting the invention in any way.

Example 1

Preparation of phenylpropioloyloxymethyl acetate 3

Figure 1:
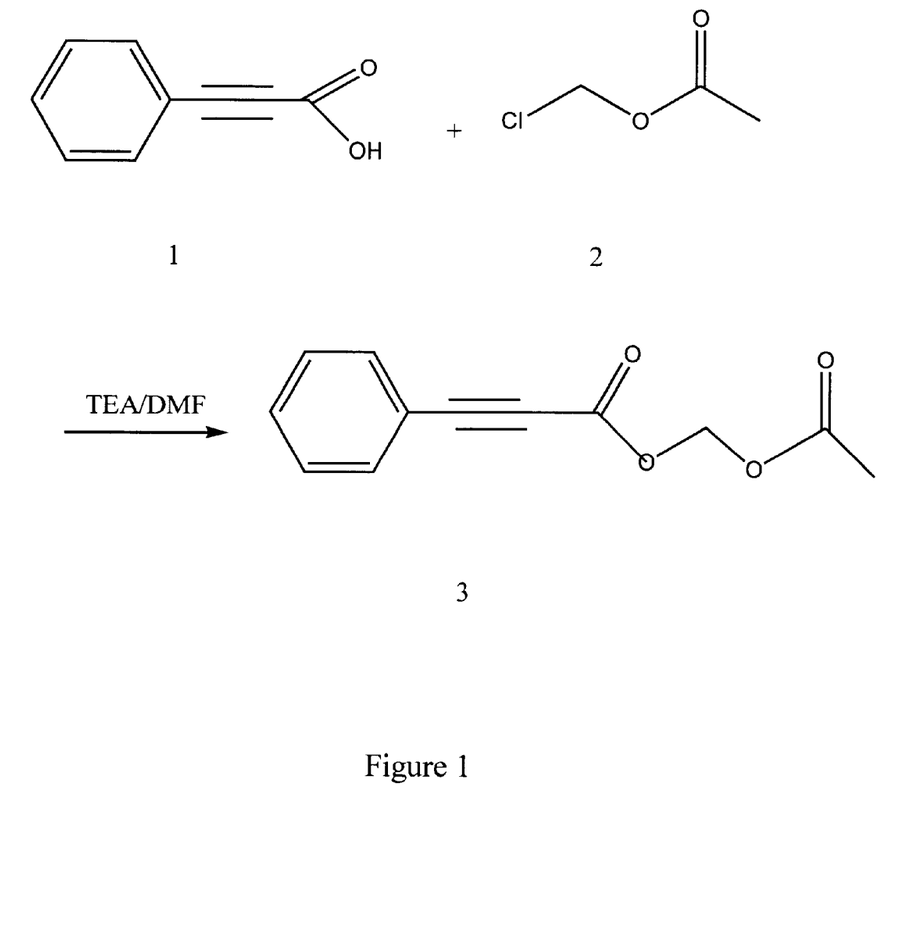
FIG. 1 shows a reaction scheme for phenylpropioloyloxymethyl acetate, prepared according to example 1.

Reference numerals correspond with those of FIG. 1.

Phenylpropiolic acid (10 g) 1 and chloromethyl acetate (7.40 g) 2 were dissolved in 30 mL of DMF; 11.4 mL of TEA was added dropwise. The reaction was stirred overnight at room temperature.

The next day GC analysis of reaction mixture showed the reaction was complete. (9.98 min; 98.6% A) The mixture was filtered and the precipitate was washed with 25 mL EtOAc. EtOAc (25 mL) was added to the filtrate, and the filtrate was washed with 50 mL of DI $H_2O$ and 25 mL portions each of the following: HCl (5% wt.), $NaHCO_3$ (sat), and NaCL (sat). The organic phase was dried over $Na_2SO_4$, filtered, and evaporated. NMR of crude product wt. 14.10. g.

The next day, Kugelrohr distillation (100–105° C. at 50 mtorr) of the crude yellow-orange material yielded 13.66 g of a light yellow liquid. DMF was still present, so the material was placed under hivac at 50° C. for an additional 30 minutes. The final wt. of the product 3 was 13.50 g.

Table 1 provides a summary of components used.

TABLE 1

| Compound | MW | moles | grams | mL | Density |
|---|---|---|---|---|---|
| phenylpropiolic acid 1 | 146.15 | 0.07 | 10.0 | — | — |
| chloromethyl acetate 2 | 108.52 | 0.07 | 7.4 | — | — |
| TEA | 101 | 0.08 | 8.3 | 11.4 | 0.726 |
| DMF | 73.09 | — | — | 26.1 | 0.940 |

Example 2

Preparation of S-benzylthioglycoloyloxymethyl acetate 5

Figure 2:
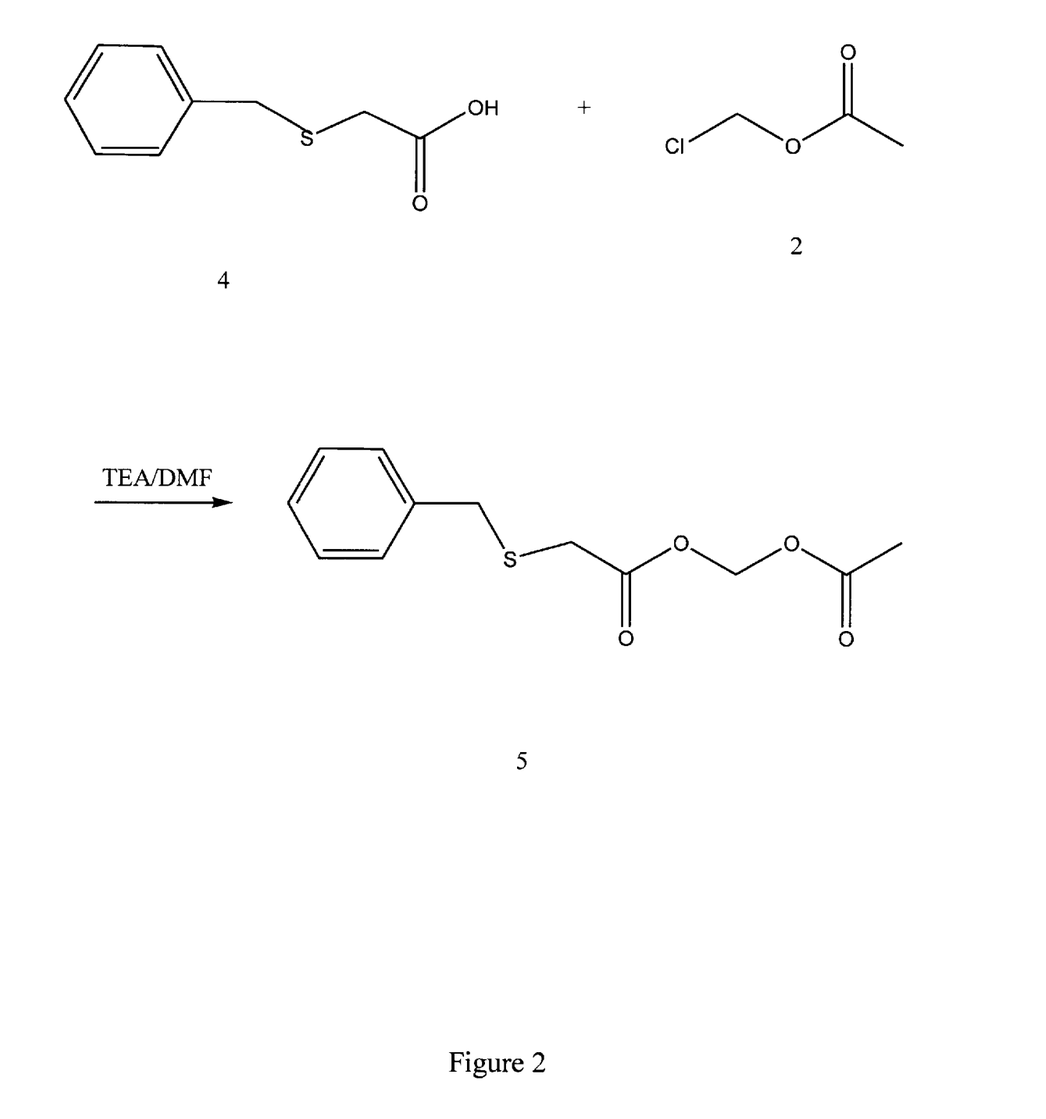
FIG. 2 shows a reaction scheme for S-benzylthioglycoloyloxymethyl acetate, prepared according to Example 2.

Reference numerals correspond with those of FIG. 2.

A solution of 10 g of S-benzylthioglycolic acid 4 and 6 g of chloromethyl acetate 2 in 50 mL of DMF was treated with 9.2 mL of TEA; the resulting solution was stirred overnight at room temperature.

The next day the reaction mixture was filtered to remove TEA.HCl and the filter cake was washed first with 50 mL of ethyl acetate then washed twice with water (60 mL), 5% hydrochloric acid (60 mL), sodium bicarbonate (60 mL) and brine (60 mL). The ethyl acetate layer was dried over sodium sulfate and concentrated in vacuo to afford 11.4 g of crude product. The proton NMR was perfect for the desired product 5 and GC indicated a high degree of purity.

The following day the product was distilled in a Kugelrohr at 130–135° C. and 0.05 Torr to afford 11.2 g (80%) of product. The proton and carbon were perfect for the desired product 5. GC indicated 100% purity.

Table 2 provides a summary of components used.

TABLE 2

| Compound | MW | moles | grams | mL | Density |
|---|---|---|---|---|---|
| S-benzylthioglycolic acid 4 | 182.24 | 0.05 | 10.0 | — | — |
| chloromethyl acetate 2 | 108.52 | 0.05 | 6.0 | — | — |
| TEA | 101 | 0.07 | 6.7 | 9.2 | 0.726 |
| DMF | — | — | — | 50 | — |

Example 3

Preparation of 3-(phenylthio)acryloyloxymethyl acetate 7

Figure 3:
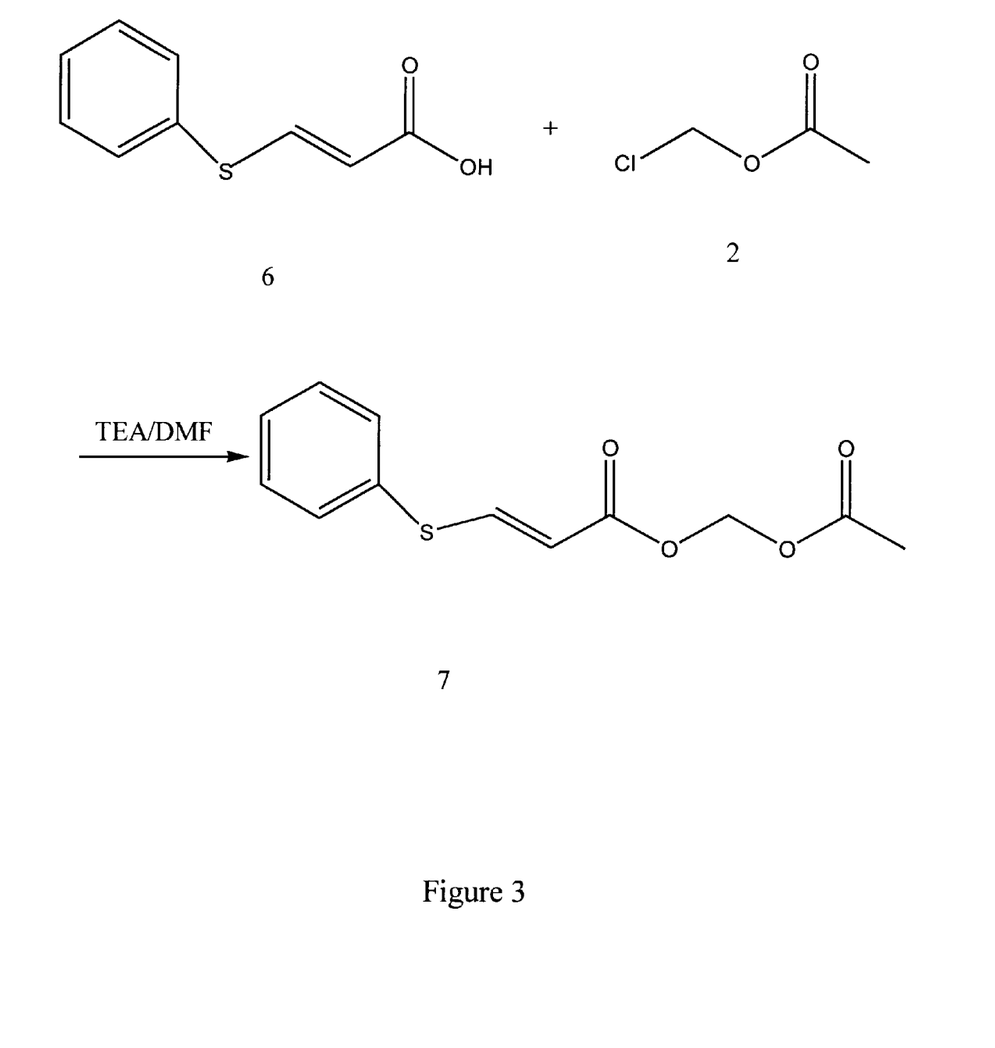
FIG. 3 shows a reaction scheme for 3-(phenylthio)acryloyloxymethyl acetate, prepared according to Example 3.

Reference numerals correspond with those of FIG. 3.

3-(phenylthio)acrylic acid (10 g) 6 and chloromethyl acetate (6.0 g) 2 were dissolved in 25 mL of DMF; 9.3 mL of TEA was added dropwise. The reaction was stirred overnight at room temperature.

The next day, GC analysis of the reaction mixture showed a mixture of two products (11.33 min, 63.5% A; 10.82 min., 35.2% A). A GC trace of the starting acid showed a 1:2 mixture of compounds. The mixture was filtered and the precipitate was washed with 25 mL EtOAc. EtOAc (25 mL) was added to the filtrate, and the filtrate was washed with 50 mL of DI $H_2O$, and 25 mL portions each of the following: HCl (5% wt.), $NaHCO_3$ (sat), and NaCL (sat). The organic phase was dried over $Na_2SO_4$, filtered, and evaporated. The NMR crude product wt. was 13.64 g.

The next day Kugelrohr distillation (125–130° C. at 50 mtorr) of the crude yellow-orange material 7 yielded 12.91 g of a light yellow liquid.

Table 3 provides a summary of compounds used.

TABLE 3

| Compound | MW | moles | grams | mL | Density |
|---|---|---|---|---|---|
| 3-(phenylthio)acrylic acid 6 | 180.23 | 0.06 | 10.0 | — | — |
| chloromethyl acetate 2 | 108.52 | 0.06 | 6.0 | — | — |
| TEA | 101 | 0.07 | 6.7 | 9.3 | 0.726 |
| DMF | 73.09 | — | — | 21.2 | 0.940 |

Example 4

Preparation of 4-cyclohexylbutanoyloxymethyl acetate 9

Figure 4:
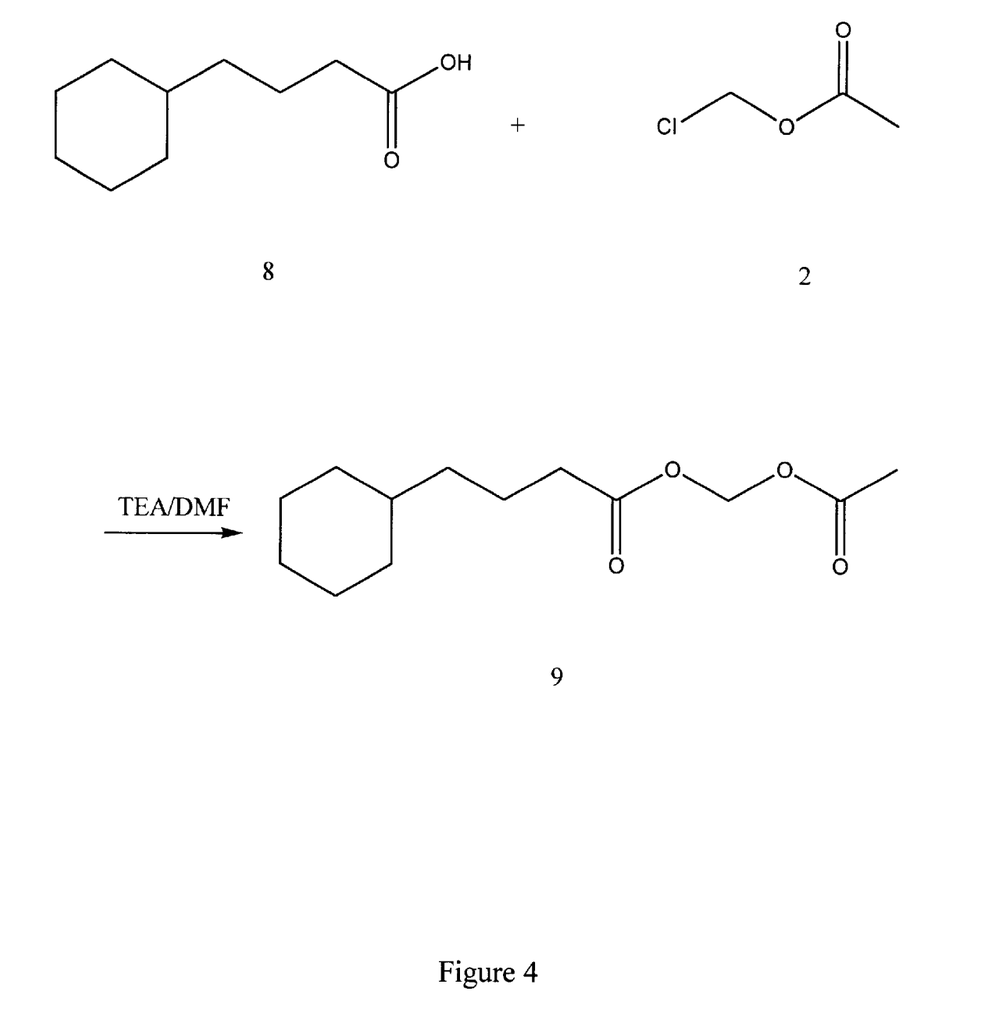
FIG. 4 shows a reaction scheme for 4-cyclohexanebutyroyloxymethyl acetate, prepared according to Example 4.

Reference numerals correspond with those of FIG. 4.

4-cyclohexanebutyric acid (10.0 g) 8 and chloromethyl acetate (6.4 g) 2 were dissolved in 25 mL of DMF; TEA (10.0 mL) was added dropwise over 10 minutes. The reaction mixture was stirred overnight at room temperature.

The next day GC analysis indicated the reaction was approximately two-thirds complete (acid 7.60 min., 33.9% A; oxymethyl acetate 9.36 min., 66.1% A). The reaction was stirred overnight.

The following day GC analysis indicated a complete reaction (acid 7.71 min., 6.26% A; oxymethyl acetate 9.51 min., 90.48% A). The mixture was filtered; the precipitate was washed with 25 mL of EtOAc. 50 mL of EtOAc was added to the filtrate and the organic phase was washed with 1×50 mL of DI H$_2$O. The organic phase was then washed with a single 25 mL portion of each of the following: 5% wt. HCl, NaHCO$_3$ (sat), and NaCl (sat), then dried over Na$_2$SO$_4$ (anhy). Evaporation of solvent afforded 12.42 g of a clear liquid. NMR showed DMF. Kugelrohr distillation at 90–95° C. and 65 mtorr yielded 10.35 g of a clear liquid 9. NMR; GC; C13 NMR pkg. wt. 10.06 g.

Table 4 provides a summary of compounds used.

TABLE 4

| Compound | MW | moles | grams | mL | Density |
| --- | --- | --- | --- | --- | --- |
| 4-cyclohexanebutyric acid 8 | 170.25 | 0.06 | 10.0 | — | — |
| chloromethyl acetate 2 | 108.52 | 0.06 | 6.4 | — | — |
| TEA | 101 | 0.07 | 7.1 | 9.8 | 0.726 |
| DMF | 73.09 | — | — | 22.4 | 0.940 |

Example 5

Preparation of 6-phenyl-3 5-hexadienoyloxymethyl acetate 11

Figure 5:
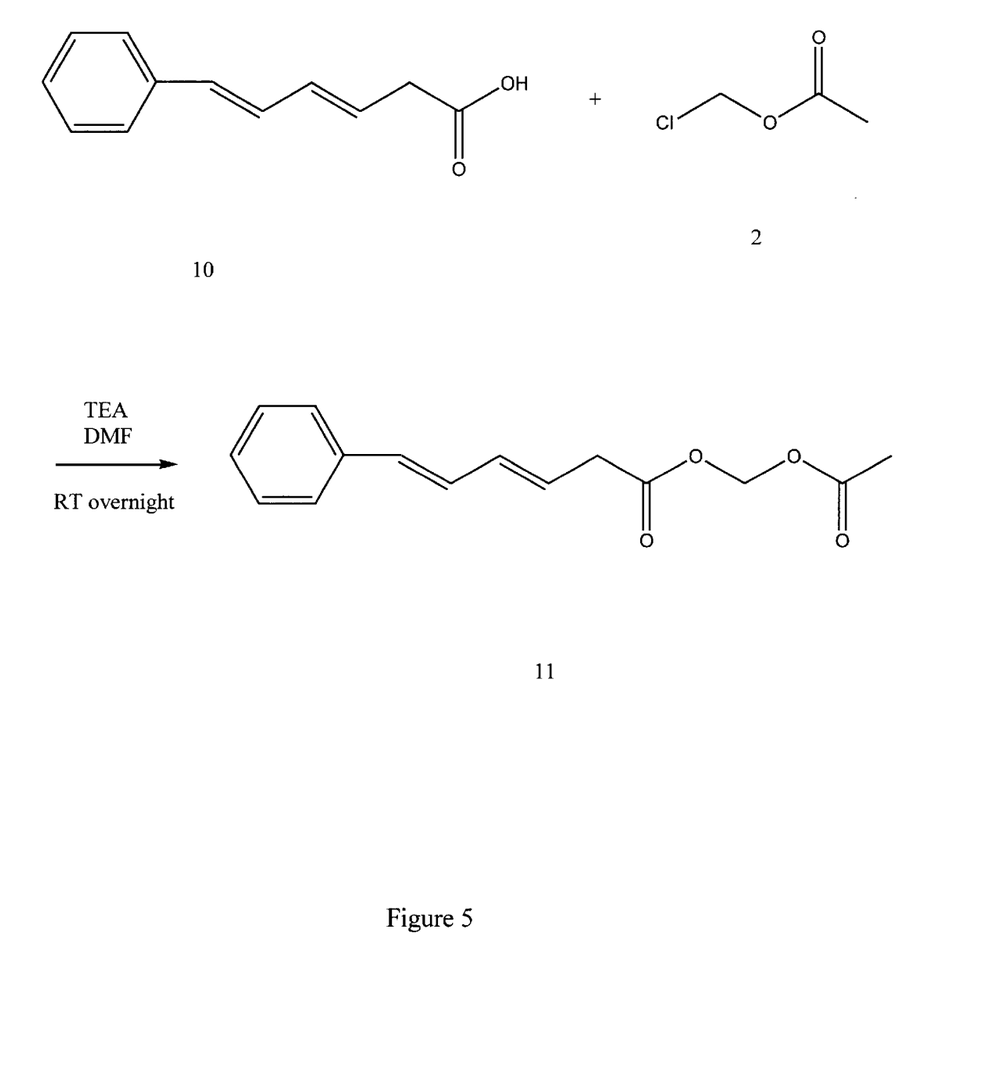
FIG. 5 shows a reaction scheme for 6-phenyl-3,5-hexadienoyloxymethyl acetate, prepared according to Example 5.

Reference numerals correspond to those in FIG. 5.

A solution of 7 g of 6-phenyl-3,5-hexadienoic acid 10 and 4 g of chloromethyl acetate 2 was dissolved in 25 mL of DMF; 6.2 mL of TEA was added dropwise over 20 minutes. The resulting solution was stirred at room temperature and monitored by TLC. The reaction was stirred overnight at room temperature.

The next day, after 20 hours at room temperature, the total precipitated TEA.HCl was 4.8 g versus 5.5 g theoretical. The reaction was stirred for another four hours and there was no further precipitate. The reaction mixture was partitioned between 100 mL of ethyl acetate and 50 mL of water. The aqueous layer was acidified and extracted with ethyl acetate, dried over sodium sulfate and concentrated in vacuo to afford 0.6 g of the starting acid. The ethyl acetate extracts from above were washed with 50 mL each of 5% hydrochloric acid, saturated sodium bicarbonate and brine, dried over sodium sulfate and concentrated in vacuo to afford 7.7 g of a red orange oil 11. The TLC (1:1 hexane:ethyl acetate) showed two distinct isomers except that the Rfs were very similar. The NMR showed that three isomers are present but that the E,E isomer predominates.

The following day the oil was dissolved in 20 mL of ethyl acetate and hexanes were added until it was just turbid (20 mL). Enough EtOAc (<1 mL) was added to get the solution clear and then it was charged onto a Biotage 75S column.

The solution was eluted with 90:10 hexane ethyl acetate. Because of the need to use 1:1 ethyl acetate to solubilize the material, elution began in the second fraction. Better separation of the isomers might be possible if not for the insolubility in the elution solution.

Fraction 2–3 by TLC appeared to contain almost equal amounts of the E,E- and E,Z-isomer while a third unidentified isomer was also present. This fraction weighed less than 0.1 g and was discarded.

Fractions 4–11 were a mixture of three isomers with the E,E-isomer accounting for around 75–80% of the total. The E,Z-isomer was too small to even integrate although it is still present. The proton and carbon NMRs were perfect for the above product. The yield of these fractions was 3.5 g.

Fraction 12 appeared by TLC to be the E,E isomer but upon concentration and NMR analysis it was found to contain about 15% E,Z. The yield was about 0.3 g.

Fraction 13 was mostly the E,E-isomer although a trace of E,Z- could be seen by NRM. The carbon NMR was perfect for the desired E,E-isomer but there was less than 0.1 g. Fractions 12 and 13 were combined.

Table 5 provides a summary of components used.

TABLE 5

| Compound | MW | moles | grams | mL | Density |
| --- | --- | --- | --- | --- | --- |
| 6-phenyl-3,5-dienoic acid 10 | 188.22 | 0.04 | 7.0 | — | — |
| chloromethyl acetate 2 | 108.52 | 0.04 | 4.0 | — | — |
| TEA | 101 | 0.04 | 4.5 | 6.2 | 0.726 |
| DMF | — | — | — | 25 | — |

Example 6

Preparation of 5-phenyl-2,4-pentadienoyloxymethyl acetate 13

Figure 6:
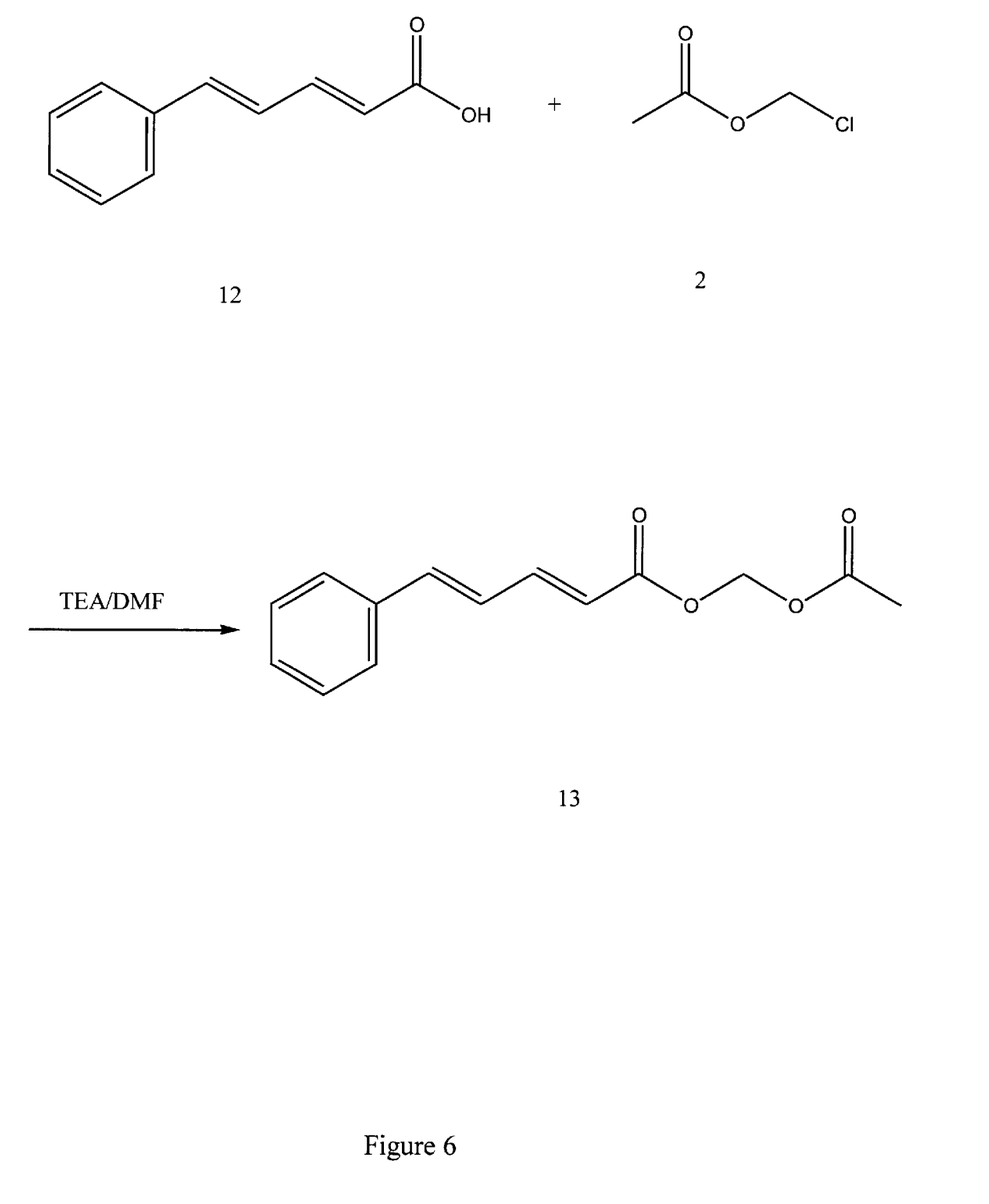
FIG. 6 shows a reaction scheme for 5-phenyl-2,4-pentadienoyloxymethyl acetate, prepared according to Example 6.

Reference numerals correspond to those in FIG. 6.

5-phenylpentadienoic acid (7.5 g) 12 and chloromethyl acetate (4.3 g) 2 were dissolved in 25 mL of DMF; TEA (6.7 mL) was added dropwise over 10 minutes. The reaction mixture was stirred overnight at room temperature.

The next day the precipitate that formed overnight was collected by filtration and washed with 25 mL of ethyl acetate. The filtrate was partitioned between 50 mL each of water and ethyl acetate. The ethyl acetate layer was washed with 25 mL each of 5% hydrochloric acid, saturated sodium bicarbonate and brine, dried over sodium sulfate and concentrated in vacuo to afford 8.1 g of a liquid which by NMR was largely the desired product 13. GC and TLC analysis showed very minor impurities (>95% pure).

The following day the crude product was taken up in 10 mL of chloroform and loaded onto a Biotage 40M column and eluted with chloroform. Fractions 7–29 were combined and concentrated in vacuo to afford 5.8 g of a mobile liquid. The proton and carbon were perfect for the desired product 13.

Table 6 provides a summary of components used.

TABLE 6

| Compound | MW | moles | grams | mL | Density |
| --- | --- | --- | --- | --- | --- |
| 5-phenylpentadienoic acid 12 | 188.22 | 0.04 | 7.5 | — | — |
| chloromethyl acetate 2 | 108.52 | 0.04 | 4.3 | — | — |
| TEA | 101 | 0.05 | 4.8 | 6.7 | 0.726 |
| DMF | — | — | — | 25 | — |

Example 7

Preparation of cinnamoyloxymethyl acetate 15

Figure 7:
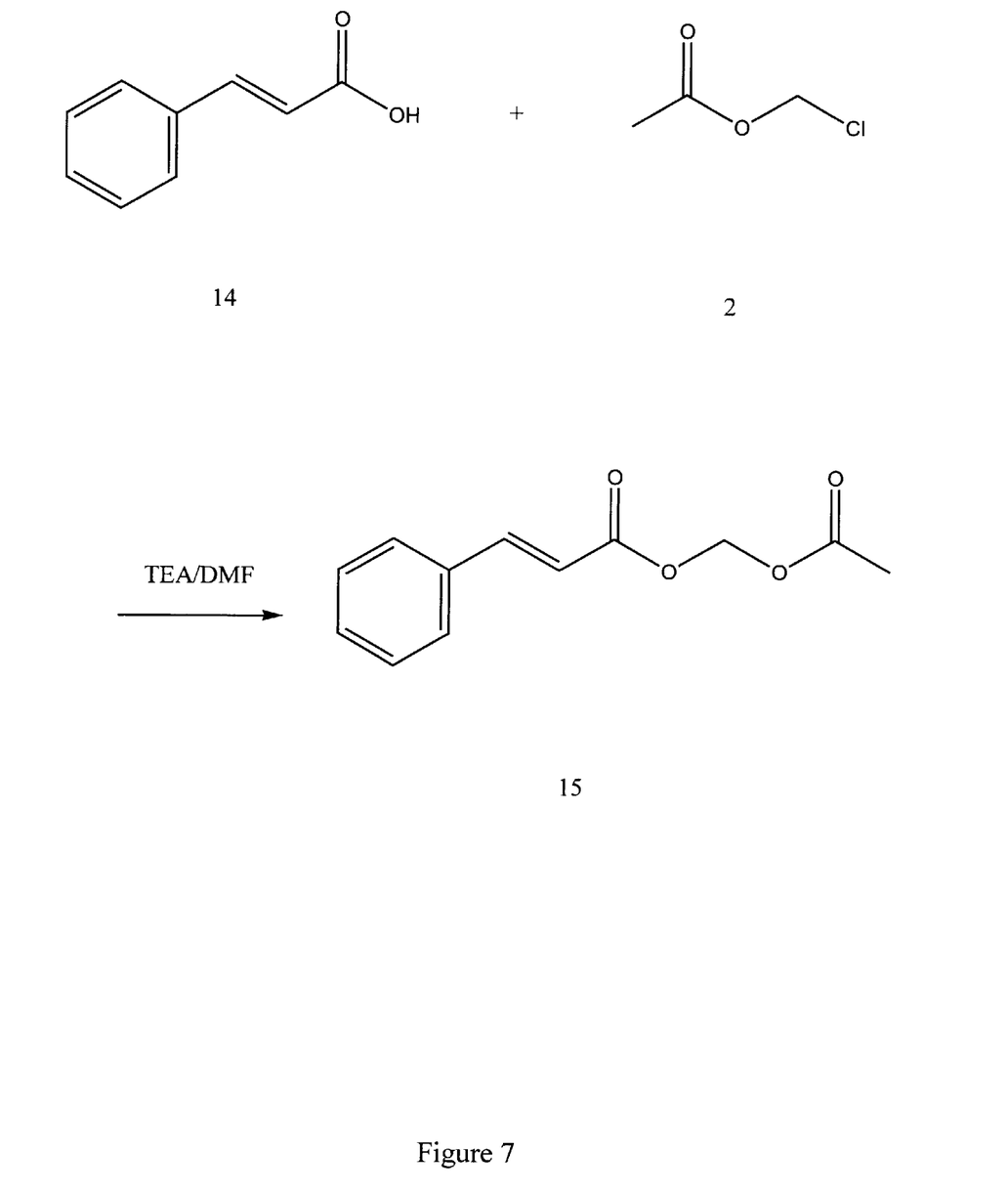
FIG. 7 shows a reaction scheme for cinnamoyloxymethyl acetate, prepared according to Example 7.

Reference numerals correspond with those of FIGS. 6 and 7.

Cinnamic acid (10 g) 14 and chlormethyl acetate (7.3 g) 2 were dissolved in 25 mL of DMF; 11.3 mL of TEA was added dropwise. The reaction was stirred overnight at room temperature.

A precipitate formed overnight. The reaction mixture was analyzed by GC and only a single signal was present. The reaction mixture was filtered and the filter cake was washed with 25 mL of ethyl acetate. The filtrate was partitioned between 50 mL each of water and ethyl acetate. The ethyl acetate layer was washed with 25 mL each of 5% hydrochloric acid, saturated sodium bicarbonate and brine, dried over sodium sulfate and concentrated in vacuo to afford a liquid which by NMR was largely the desired product 15.

The next day the reaction mixture was distilled via Kugelrohr at 90–100° C. and 0.2 Torr to afford 11.9 g of a clear liquid. The proton and carbon were perfect for the desired product 15. The GC indicated 100% purity.

Table 7 provides a summary of components used.

TABLE 7

| Compound | MW | moles | grams | mL | Density |
|---|---|---|---|---|---|
| cinnamic acid 14 | 148.16 | 0.07 | 10.0 | — | — |
| chloromethyl acetate 2 | 108.52 | 0.07 | 7.3 | — | — |
| TEA | 101 | 0.08 | 8.2 | 11.3 | 0.726 |
| DMF | — | — | — | 25.8 | — |

Example 8

Compounds prepared according to Examples 1–7 were tested for anti-proliferation against PC-3 prostate breast cancer cells. Butyric acid and trichostatin, a potent HDAC inhibitor, were used as reference compounds. Both compounds were purchased from Sigma-Aldrich, Milwaukee, Wis.

The PC3 cell line was maintained in RPMI supplemented with 10% fetal calf serum and antibiotics. The EDR assay was performed as described by Kern and Weisenthal in "Highly Specific Prediction of Antineoplastic Drug Resistance With An In Vitro Assay Using Suprapharmacologic Drug Exposures," *J. Nat. Cancer Inst.*, 82:582–588 (1990); and Fruehauf and Bosanquet, "In vitro Determination of Drug Response: A Discussion of Clinical Applications," *PPO Updates* 7(12):1–16 (1993). Cells were suspended in 0.12% soft agar in complete medium and plated (2,000 cells per well, as determined by preliminary experiments) in different drug concentrations onto a 0.4% agarose underlayer in 24-well plates. Plating cells on agarose underlayers supports the proliferation only of the transformed cells, ensuring that the growth signal stems from the malignant component of the tumor.

All compounds were dissolved in DMSO to 200× stock solutions. Stock solutions were diluted to 20× working solutions using the tissue culture medium, serially diluted and added to the 24-well plates. The concentration range was 0.001 $\mu$M to 0.3 $\mu$M for trichostatin and 10 $\mu$M–1,000 $\mu$M for the other compounds. No significant changes in pH of the culture medium were observed under the above conditions. Diluent control wells contained PC3 cells treated with DMSO, at the dilutions used for appropriate drug treatment. All experimental points were represented by two separate wells (duplicates). Positive controls were determined using at least two wells treated with an extremely high dose of cisplatin, an anti-cancer agent. Four wells containing tumor cells that were not treated with drugs served as negative controls in each experiment.

Cells were incubated with drugs under standard culture conditions for five days. Cultures were pulsed with tritiated thymidine ($^3$H-TdR, New Life Science Products, Boston, Mass.) at 5 $\mu$Ci per well for the last 48 hours of the culture period. Cell culture plates were then heated to 90° C. to liquefy the agarose, and cells were harvested onto glass fiber filters, which were then placed into counting vials containing liquid scintillation fluid. The radioactivity trapped on the filters was counted with a Beckman scintillation counter. The fraction of surviving cells was determined by comparing $^3$H-TdR incorporation in treated (experimental points) and untreated (negative control) wells. All drug concentrations are presented as $\mu$M, allowing for normalization of drug response curves and direct comparison of the effects of the drugs. Microsoft Excel was used to organize the raw data on EDR experiments, and the SigmaPlot program was utilized to generate drug response curves. All drug response curves were as approximated as sigmoidal equations (characteristic for typical drug response curves) to fit the data. IC$_{50}$ values were determined using the approximated sigmoidal curves and expressed as $\mu$M.

Table 8 provides the PC-3 IC$_{50}$ data for each of the compounds tested.

TABLE 8

| COMPOUND | PC-3 IC$_{50}$ ($\mu$M) |
|---|---|
| phenylpropioloyloxymethyl acetate | 25 |
| S-benzylthioglycoloyloxymethyl acetate | 28.4 |
| 3-(phenylthio)acryloyloxymethyl acetate | 30 |
| 4-cyclohexanebutyroyloxymethyl acetate | 23.2 |
| 6-phenyl-3,5-hexadienoyloxymethyl acetate | 18 |
| 5-phenyl-2,4-pentadienoyloxymethyl acetate | 20 |
| cinnamoyloxymethyl acetate | 12.5 |
| butyric acid | >2000 |
| trichostatin | 0.005 |

As can be seen from Table 8, the results demonstrate that the compounds of the present invention possess superior activity as compared to butyric acid.

Whereas particular embodiments of this invention have been described above for purposes of illustration, it will be evident to those skilled in the art that numerous variations of the details of the present invention may be made without departing from the invention as defined in the appended claims.

What is claimed is:

1. A compound having formula (1):

$$\text{(1)}$$

wherein R is unsubstituted (C$_2$–C$_{10}$ alkenyl, substituted or unsubstituted C$_2$–C$_{10}$ alkynyl, or has the general formula (2):

$$\text{(2)}$$

wherein Z is selected from the group consisting of hydrogen, substituted or unsubstituted aryl, heteroaryl, cycloalkyl having the formula C$_n$H$_{2n-1}$, and alkoxyl;

wherein n is 3 or greater;

wherein X is S, O, C=O or CH$_2$;

wherein R$_1$ is S, O, CH=CH or C≡C;

wherein R$_2$ is CH$_2$, CH=CH or C≡C; and wherein o, p and q are the same or different and are each between 0 and 10, but when o is zero and R$_1$ R$_2$ is CH=CH or C≡C, Z is not hydrogen or alkoxy; but when o, p and q are zero, Z is not alkoxy.

2. The compound of claim 1, wherein R is C$_6$H$_5$—C≡C—.

3. The compound of claim 1, wherein R is C$_6$H$_5$—CH$_2$—S—CH$_2$—.

4. The compound of claim 1, wherein R is C$_6$H$_5$—S—CH=CH—.

5. The compound of claim 1, wherein R is C$_6$H$_{11}$—(CH$_2$)$_3$—.

6. A compound having the formula:

7. A compound having the formula:

8. A compound having the formula:

9. A compound having the formula (1):

(1)

wherein R is unsubstituted $C_2$–$C_{10}$ alkenyl, $C_2$–$C_{10}$ alkynyl, or has the general formula (2):

(2)

wherein Z is selected from the group consisting of substituted or unsubstituted aryl, heteroaryl, and cycloalkyl having the formula $C_nH_{2n-1}$;

wherein n is 3 or greater;

wherein X is S, O, C=O or $CH_2$;

wherein $R_1$ is S, O, CH=CH or C≡C;

wherein $R_2$ is $CH_2$, CH=CH or C≡C; and wherein o, p and q are the same or different and are each between 0 and 10.

* * * * *